(12) United States Patent
Yun et al.

(10) Patent No.: US 7,090,977 B2
(45) Date of Patent: Aug. 15, 2006

(54) ELECTROCHEMILUMINESCENCE DETECTION METHOD FOR NUCLEIC ACID USING INTERCALATOR AND TRANSITION METAL COMPLEX

(75) Inventors: Kyu-Sik Yun, Seoul (KR); Jeong-Gun Lee, Kyunggi-Do (KR); Je-Kyun Park, Seoul (KR); Su-Hyeon Kim, Seoul (KR); Sang-Eun Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 630 days.

(21) Appl. No.: 10/282,251

(22) Filed: Oct. 29, 2002

(65) Prior Publication Data

US 2003/0092055 A1 May 15, 2003

(30) Foreign Application Priority Data

Oct. 30, 2001 (KR) ............... 10-2001-0067230

(51) Int. Cl.
*C12Q 1/68* (2006.01)
(52) U.S. Cl. .......................... 435/6; 436/94

(58) Field of Classification Search ................ 435/6; 436/94
See application file for complete search history.

(56) References Cited

U.S. PATENT DOCUMENTS

| | | | |
|---|---|---|---|
| 5,776,672 A * | 7/1998 | Hashimoto et al. ............ 435/6 |
| 6,221,586 B1 * | 4/2001 | Barton et al. .................. 435/6 |
| 6,342,359 B1 * | 1/2002 | Lee et al. ...................... 435/6 |
| 6,635,426 B1 * | 10/2003 | Pak et al. ...................... 435/6 |
| 6,649,350 B1 * | 11/2003 | Barton et al. .................. 435/6 |
| 2002/0106682 A1 * | 8/2002 | Lee et al. ...................... 435/6 |
| 2002/0117396 A1 * | 8/2002 | Pak et al. .................... 204/418 |

* cited by examiner

*Primary Examiner*—Kenneth R. Horlick
(74) *Attorney, Agent, or Firm*—Fleshner & Kim, LLP

(57) ABSTRACT

Disclosed is a method for detecting nucleic acid hybridization by using intercalator binding to hybridized nucleic acid, wherein oxidation-reduction of transition metallic complex is induced to cause electrochemiluminescence, thereby providing a method for detecting nucleic acid hybridization without a special labeling.

10 Claims, 5 Drawing Sheets

Tri(2,2-bipyridyl)ruthenium(II) complex
Ru(bpy)$_3^{2+}$

Tris(2,10-biphenanthroline)ruthenium(II) complex
Ru(phen)$_3^{2+}$

Daunorubicin ($R_1$=H, $R_2$=H, $R_3$=OH, $R_4$=H)

Doxorubicin ($R_1$=OH, $R_2$=H, $R_3$=OH, $R_4$=H)

ELECTROCHEMILUMINESCENCE DETECTION METHOD FOR NUCLEIC ACID USING INTERCALATOR AND TRANSITION METAL COMPLEX

BACKGROUND OF THE INVENTION

1. Field of the Invention

The present invention relates to a method for detecting nucleic acid hybridization, in which electrochemiluminescence is promoted by using intercalator which is peculiarly binding only to double-stranded nucleic acid.

2. Description of the Background Art

Methods for detecting a result of nucleic acid hybridization generally include nucleic acid hybridization detection methods by a radioautography, a laser-induced fluorescence (LIF) and an electrochemical method.

The radioautography method which detects nucleic acid hybridization by labeling target nucleic acid as radioactive isotope is the most widely used in molecular biology. $^{32}P$ is used as the radioactive isotope, and photographic films are used to detect a binding state of target oligonucleotide and probe oligonucleotide which are labeled. The radioautography method does not require much basic knowledge, thereby easily being applied. However, the radioautography method has several disadvantages that long analysis time such as several hours and a day makes it impossible to know a result fast, a resolution ability is low with orders of 0.1~10 μm, and radioactive isotope used in excitation is not stable.

Recently, a laser-induced fluorescence (LIF) method is much used in DNA hybridization detection because several kinds of fluorescence material is used, a resolution ability is excellent, and a result is immediately known. Nowadays, if a charge coupled device (CCD) camera to which fluorescence analysis and image technique are combined is introduced, molecules labeled as fluorescence materials can be imaged real time. However, said method also has several disadvantages that DNA of a sample has to be labeled as fluorescence material before measuring the DNA of a sample, a process to separate and refine the DNA is complicated, a stability for experiments is required, and expensive equipments such as a laser and an attached device for optical detection and an expensive image scanner for scanning a two-dimensional substrate are required.

The method for detecting DNA hybridization by an electrochemical method is one to detect DNA hybridization by using a binding of metallic complex having activity electrochemically and double-stranded DNA. Even if the method is enough simple to provide a cheap detection apparatus, sensitivity is not good.

Since the aforementioned conventional methods for detecting nucleic acid hybridization have several disadvantages, a new detecting method having a high sensitivity is necessary. Especially, a development of a small and cheap system for detecting nucleic acid fast without a process that a sample is bound to label material is required as a portable diagnosis device.

SUMMARY OF THE INVENTION

Therefore, an object of the present invention is to provide a method for detecting nucleic acid hybridization having simplification and excellent detection sensitivity without a separate labeling process, in which electrochemiluminescence is caused by inducing an oxidation-reduction reaction between intercalator and transition metallic complex.

An object of the present invention is to provide a method for detecting nucleic acid hybridization, comprising steps of applying proper voltage and using intercalator of nucleic acid to induce an electrochemiluminescence reaction of transition metallic complex; and detecting the quantity of light generated thereby, wherein the intercalator peculiarly binds to double-stranded nucleic acid which is formed by hybridization between probe nucleic acid fixed on a metal surface and target nucleic acid in solution and causes an electrochemiluminescence reaction by inducing an oxidation-reduction reaction of transition metallic complex. The above intercalator can be selected from the group consisting of doxorubicin, daunorubicin and DAPI(4',6-Diamidino-2-phenylindole).

Another object of the present invention is to provide a novel use of DAPI as an effective intercalator, The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
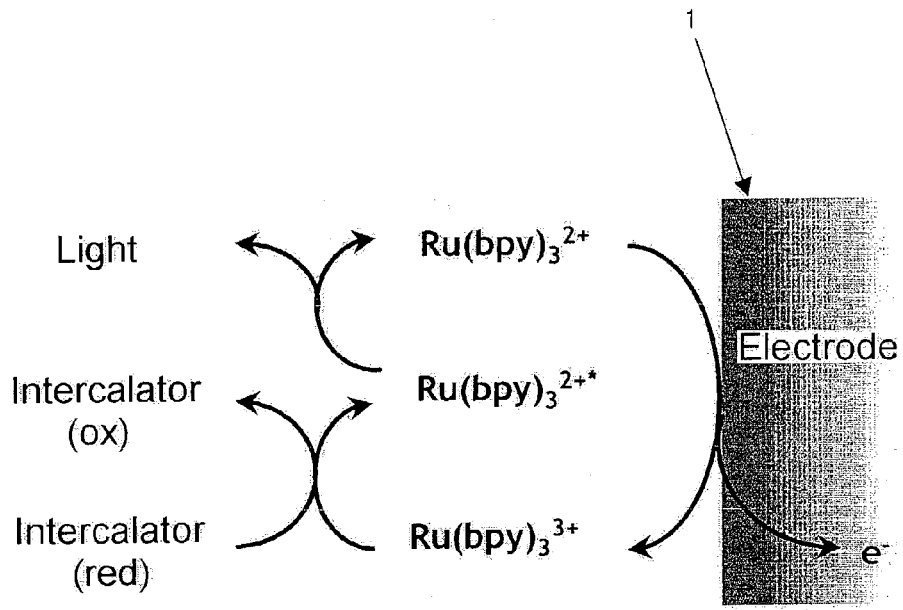
FIG. 1 shows a principle of electrochemiluminescence by intercalator, in which 1 indicates a working electrode.

Reference will now be made in detail to the preferred embodiments of the present invention, examples of which are illustrated in the accompanying drawings.

The method for detecting nucleic acid hybridization according to the present invention can be applied to a method for a method for detecting nucleic acid hybridization on a nucleic acid detector such as a nucleic acid array, a nucleic acid sensor, a nucleic acid chip, etc.

The nucleic acid to be detected in the present invention includes oligonucleotide, DNA, RNA, PNA, cDNA, etc. The aforementioned nucleic acid detector which arranges nucleic acid fragment having various base sequences on a narrow substrate as high density is used to detecting information for nucleic acid in the unknown sample by hybridizing probe nucleic acid fixed thereon with target nucleic acid of an unknown sample having a complementary base sequence for the probe nucleic acid. The hybridization means that subsequences having a complementary base sequence are binding to one another to form double-stranded nucleic acid, by hydrogen bond between adenine-thymine or guanine-cytosine which constitute nucleic acid bases. The probe nucleic acid is a single strand nucleic acid complementary to the target nucleic acid.

Intercalator used in the detecting method of the present invention peculiarly binds to double-stranded nucleic acid formed by hybridization between probe nucleic acid fixed on a surface such as a nucleic acid array and target nucleic acid in sample solution, and induces oxidation-reduction reaction of transition metallic complex to cause an electrochemiluminescence reaction. An object of the present invention is to provide an effective nucleic acid sensor detecting method by the intercalator.

That is, the object of the present invention is to provide a method for detecting nucleic acid hybridization on a nucleic acid sensor by selecting intercalator which induces oxidation-reduction reaction of transition metallic complex to cause electrochemiluminescence, among several intercalators peculiarly binding to double-stranded nucleic acid and using the same. According the present invention, a detection method for a portable nucleic acid sensor which is fast, cheap, and simple without a separate labeling work, can be provided.

The present invention relates to a method for detecting nucleic acid hybridization by using intercalator, in which electroluminescence by transition metallic complex not using the intercalator is excluded in a detection object.

To achieve these and other advantages and in accordance with the purpose of the present invention, as embodied and broadly described herein, there is provided a method for detecting nucleic acid hybridization comprising the steps of:
 (1) fixing probe nucleic acid having thiol group on the position of 5'-phosphate on a surface of working electrode in a reaction container;
 (2) washing the surface of working electrode to which the probe nucleic acid is fixed, with phosphoric acid solution and immersing into buffer solution including target nucleic acid having base sequences complimentary to the probe nucleic acid, to perform hybridization;
 (3) adding buffer solution having dissolved intercalator to the hybridized nucleic acid, to bind the intercalator to the hybridized double-stranded nucleic acid;
 (4) removing unbinding intercalator by washing with the buffer solution;
 (5) putting the working electrode, on which hybridization and intercalator binding are performed, in the measurement container, adding transition metallic complex dissolved in the buffer solution, and installing a reference electrode and a counter electrode; and
 (6) applying a voltage on the electrodes and inducing oxidation-reduction reaction of transition metallic complex by the intercalator binding to double-stranded nucleic acid, to cause an electrochemiluminescence reaction.

In the method for detecting nucleic acid hybridization, the electrochemiluminescence is detected by an optical detector and the detected light is transmitted to a PC, so that a data can be analyzed by a change of quantity of light for time.

The probe nucleic acid can be fixed on a gold electrode or a platinum electrode used as a working electrode as aforementioned, or can be fixed at a surface of a gold plate by using an additional gold plate different from the working electrode. In this case, the used-gold plate preferably has an area of 1~5 mm$^2$. A nucleic acid hybridization detecting method by fixing the probe nucleic acid on the additional gold plate is the same with the aforementioned method except that the additional gold plate is added together with the working electrode in a stage of fixing the probe nucleic acid. In case of using the additional gold plate different from the working electrode, sample processing is easy and noise generated at a detection step is decreased.

A method for using an additional gold plate different from the reference electrode comprises the steps of:
 (1) putting an additional gold plate to the reaction container and fixing probe nucleic acid having thiol group on the position of 5'-phosphate on a surface of the gold plate;
 (2) washing the gold plate, to which the probe nucleic acid is fixed, with phosphoric acid solution and immersing into buffer solution including target nucleic acid having base sequences complimentary to the probe nucleic acid, to perform hybridization;
 (3) adding buffer solution having dissolved intercalator to the hybridized nucleic acid, to bind the intercalator to the hybridized double-stranded nucleic acid;
 (4) removing unbinding intercalator by washing with the buffer solution;
 (5) putting the gold plate, on which hybridization and intercalator binding are performed, in the measurement container, adding transition metallic complex dissolved in the buffer solution, and installing a working electrode, a reference electrode and a counter electrode; and
 (6) applying a voltage on the electrodes and inducing oxidation-reduction reaction of transition metallic complex by the intercalator binding to double-stranded nucleic acid, to cause an electrochemiluminescence reaction.

The target nucleic acid corresponding to an analysis object is used as oligomer form. Also, in case the target nucleic acid is in the form of cDNA, the target nucleic acid is used with amplifying by a method such as polymerase chain reaction (PCR). In a detecting method according to the present invention, nucleic acid is not necessary to be labeled with fluorescent material in advance.

As the buffer solution, phosphate buffer saline, 5×SSC buffer or 1×SSC buffer solution can be used.

Fixation of the probe nucleic acid and hybridization of the probe nucleic acid with the target nucleic acid are performed for 8~12 hours at 37° C., and a binding of the intercalator is performed for about 30 minutes at the room temperature.

The electrochemical apparatus comprises a three-electrode system by using gold or platinum as a working electrode, Ag/AgCl as a reference electrode, and platinum wire as a counter electrode. A power supplying unit for applying a voltage between the reference electrode and the working electrode is also provided to the apparatus. Cyclic-voltammetry at the range of voltage from +0.8 to +1.3 V is detected, so as to detect a voltage which emits maximum light. When an oxidation-reduction reaction between ruthenium derivative and the intercalator is occurred, the voltage region for emitting maximum light ranges from +1.12 to +1.20 V.

A constant applied voltage ranged from +1.12 to +1.20 V is used between the reference electrode and the working electrode in the three-electrode system. If a voltage in the above range is applied, bivalent ion of transition metal in solution is oxidized to become trivalent ion of transition metal derivative, bivalent ion derivative of an excited state is generated by the intercalator, and red light of about 610 nm is generated at the time when the bivalent ion derivative returns to the bivalent ion derivative of a ground state. At this time, it is repeated that the transition metallic complex again returns to +2 (bivalent) state, which is again changed to oxidation state of +3 (trivalent) by an oxidation voltage applied to the electrode and reacted with the intercalator to generate light.

The part of optical detection apparatus converts changed quantity of light emitted by the transition metal into a digital signal by using a photo-counter detector in a dark box, displays emitted quantity of light for time as a graph in a PC, and stores these data.

The apparatus used for a detection according to the present invention comprises:
1) gold electrode, platinum electrode, or gold plate used as a metal surface for fixing probe nucleic acid;
2) a sample container for efficiently reacting transition metallic complex, phosphoric acid buffer solution, target nucleic acid, and intercalator;
3) a power supplying unit for applying a constant voltage for the reference electrode;
4) an electrochemical detecting unit for detecting an electrochemical reaction; and
5) an optical detector for detecting a luminescence reaction between the intercalator and the transition metallic complex.

Material used as nucleic acid intercalator in the present invention is peculiarly binding to double-stranded nucleic acid and causes oxidation-reduction reaction of the transition metallic complex. As the material for intercalator, doxorubicin, daunorubicin, nogalamycin, mitoxantrone, etc. can be used. The intercalator is binding to a minor groove of the double-stranded nucleic acid, a major groove, or base pairs, depending on its kind. Quantity of intercalator biding to nucleic acid duplex is proportional to quantity of hybridized nucleic acid on an electrode. Among said materials used as intercalator, doxorubicin and daunorubicin have an excellent ability for inducing electrochemiluminescence of the transition metallic complex. Further, in the present invention, DAPI (4',6-Diamidino-2-phenylindole) can be used as an effective intercalator for detecting nucleic acid hybridization. As the transition metallic complex, ruthenium derivative is used. At this time, the ruthenium derivative preferably includes tris(2,2'-bipyridyl) ruthenium (II) [Ru(bpy)$_3^{2+}$] and tris(1,10-phenanthroline) ruthenium (II) [Ru(bpy)$_3^{2+}$].

A basic concept of the present invention is that intercalator is binding to a double-stranded structure in which probe nucleic acid is binding to target nucleic acid, and the bound intercalator induces oxidation-reduction reaction of transition metallic complex to generate light, thereby detecting electrochemical luminescence. The electrochemiluminescence method using the intercalator is different from the conventional method in which only ruthenium is used, and provides a new nucleic acid hybridization detecting method. A process for detecting target nucleic acid will be explained with attached drawings.

As shown in FIG. 1, if a voltage is applied on the working electrode 1 in a state that intercalator is binding to double-stranded nucleic acid, Ru(bpy)$_3^{2+}$ in solution is oxidized to become Ru(bpy)$_3^{3+}$ derivative, which becomes Ru(bpy)$_3^{2+*}$ derivative of an excited state by the intercalator, and red light of about 610 nm is generated at the time when the Ru(bpy)$_3^{2+*}$ derivative returns to Ru(bpy)$_3^{2+}$ derivative of a ground state. The generated light is detected by an optical detector such as a photomultiplier tube or an avalanche photodiode.

Figure 2:
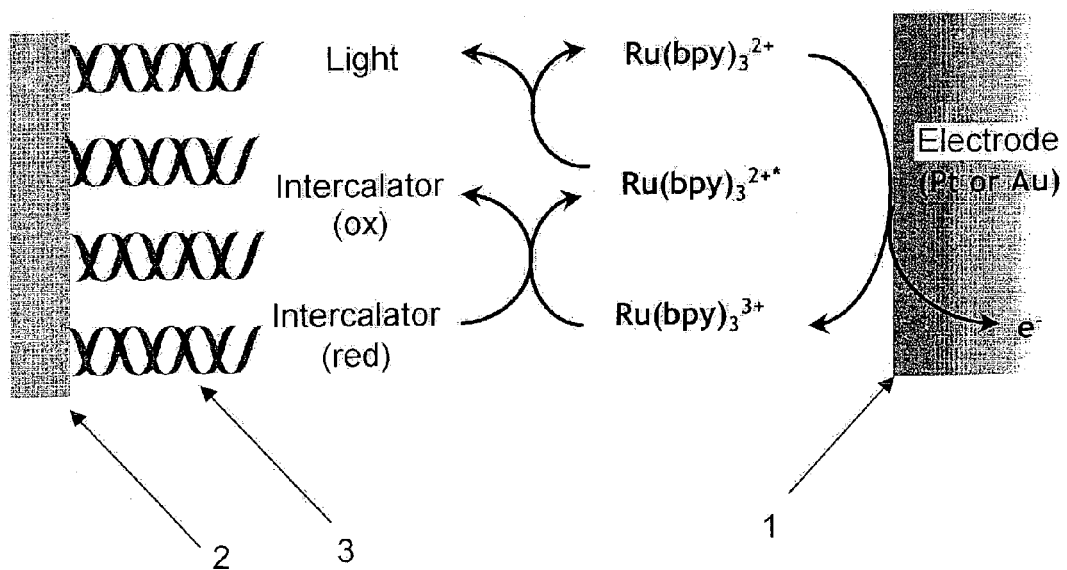
FIG. 2 shows a hybridization process between probe nucleic acid fixed on a gold plate and target nucleic acid, and a principle of electrochemiluminescence by intercalator, in which 1 indicates a working electrode, 2 indicates a gold plate, and 3 indicates double-stranded nucleic acid.
Figure 3:
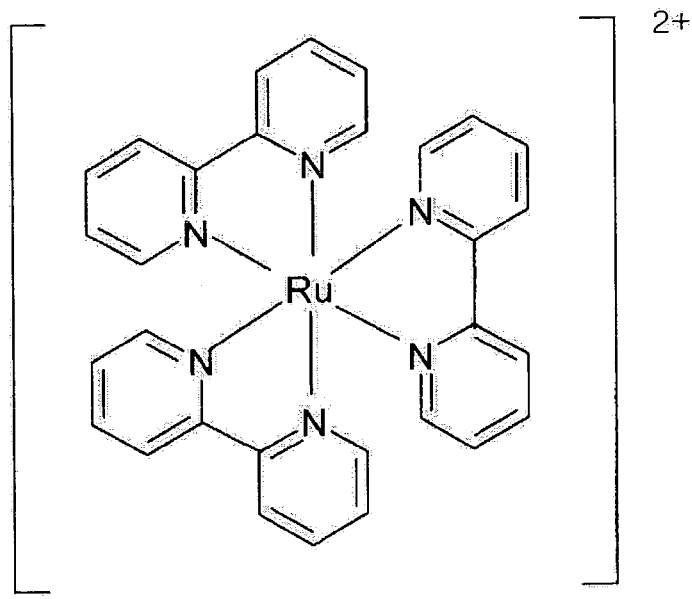
FIG. 3 shows chemical structures of Tris(2,2'-bipyridyl) ruthenium (II) [Ru(bpy)$_3^{2+}$] and Tris(1,10-phenanthroline) ruthenium(II) [Ru(phen)$_3^{2+}$], corresponding to transition metallic complex.
Figure 3:
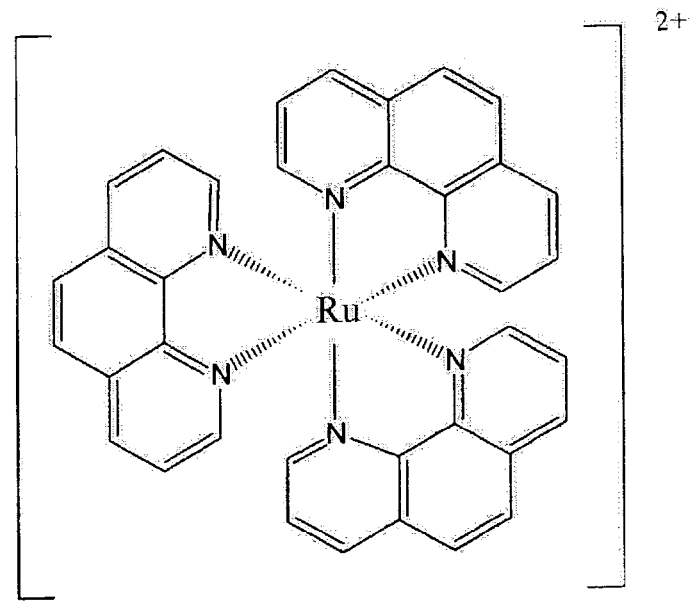
Figure 4:
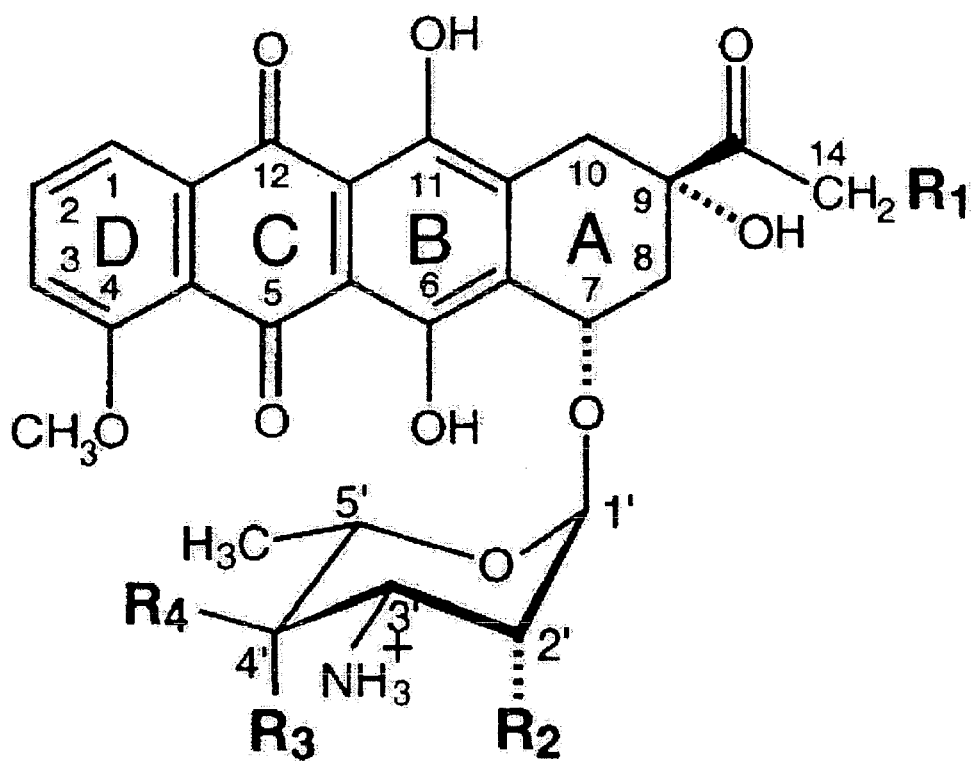
FIG. 4 shows chemical formulas of doxorubicin and daunorubicin, corresponding to intercalator.

FIG. 2 shows that probe nucleic acid is constructed as monomolecular layer by using a self-assembly method. In case of detecting hybridization by fixing the probe nucleic acid at the working electrode 1, nucleic acid at a surface of the electrode becomes unstable during a detection with an applied voltage, so that detection noise is much generated. However, if the nucleic acid is fixed by using an additional gold plate (1~5 mm$^2$) different from the working electrode, a sample process is easy and noise generated at the time of detecting is decreased. In the above process, target nucleic acid is injected and hybridized, thereby forming double-stranded nucleic acid 3. By adding intercalator to the hybridized double-stranded nucleic acid, the intercalator is binding to the nucleic acid.

Hereinafter, the present invention will be explained in detail with preferred embodiments. However, the present invention is not limited to the preferred embodiments.

FIRST PREFERRED EMBODIMENT

Doxorubicin is used as intercalator and Ru(bpy)$_3^{2+}$ is used as ruthenium derivative.

First, probe nucleic acid is fixed at a surface of a gold plate by using nucleic acid solution having thiol group on 5'-phosphate (HS-C6-5'ACTCGCAAGCACCCTAT-CAGGC 3'). For the fixation, the gold plate is put to a tube and solution including 10 μm oligonucleotide and 10 mM NaCl is put, thereby processing for one day (about 10 hours) at a temperature of 37° C. The gold plate in which oligonucletide is ascended to monomolecular layer is washed by phosphoric acid solution and immersed into 5×SSC buffer solution (sodium chloride of 750 mM, sodium citrate of 75 mM, and pH of 7.0) including 1 μm oligonucleotide having a complementary base sequence (5'-GCCTGATAGGGT-GCTTGCGAGT-3'), thereby hybridizing for one day (about 10 hours) at a temperature of 37° C. Next, doxorubicin solution of 1 mM dissolved in phosphoric acid buffer (pH 7.4) is added on the hybridized oligonucleotide, then reacted at the room temperature for about 30 minutes, thereby binding the doxorubicin to the oligonucleotide. After the reaction, the doxorubicin and the oligonucleotide are washed by 1×SSC buffer or phosphoric acid buffer solution (pH7.4), thereby removing unhybridized doxorubicin. A sample bound with doxurubicin and 1 ml Ru(bpy)$_3^{2+}$ solution dissolved in the phosphoric acid solution (pH7.4) are added to a measurement container, and a voltage of +1.19 is applied to the electrode 1 in a state that doxorubicin is binding, thereby detecting a change of quantity of light for time by an optical detector.

Figure 5:
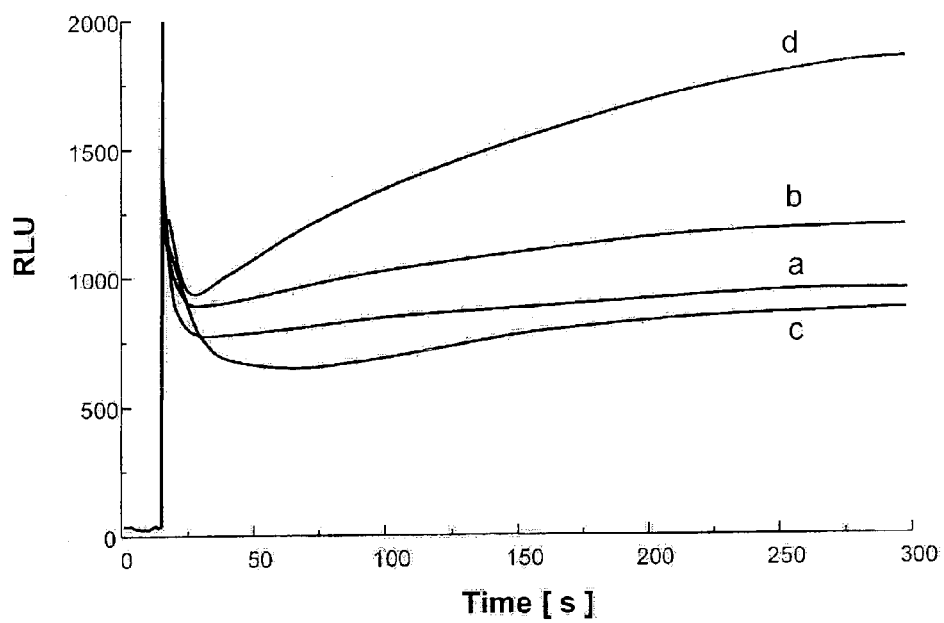
FIG. 5 shows a hybridization detection result of nucleic acid using doxorubicin and Ru(bpy)$_3^{2+}$ solution, in which a indicates quantity of light detected at a bare gold plate state, b indicates quantity of light detected when probe nucleic acid is fixed on the gold plate, c indicates quantity of light detected when probe nucleic acid is hybridized with target nucleic acid, and d indicates quantity of light detected when doxorubicin is added to the hybridized nucleic acid.

FIG. 5 shows a result of oxidation-reduction reaction between doxorubicin and $Ru(bpy)_3^{2+}$ detected by an optical detector. The FIG. 5 shows results of several cases detected in each stage such as a case that nucleic acid is not processed at the gold plate, a case that probe oligonucleotide is processed, a case that oligonucleotide is hybridized, and a case that doxtorubicin is processed.

In FIG. 5, a indicates quantity of light shown at the time when a surface of a gold plate not bound with oligonucleotide is detected at $Ru(bpy)_3^{2+}$ solution. At this time, quantity of emitted light represents quantity of light of ruthenium itself shown when a voltage is applied to ruthenium solution. In FIG. 5, b indicates quantity of light of shown when probe oligonucleotide is fixed and then detected by $Ru(bpy)_3^{2+}$ solution. At this time, quantity of emitted light is a little more than that emitted from ruthenium itself, which is resulted from a reciprocal reaction between ruthenium and probe oligonucleotide. c indicates quantity of light detected by $Ru(bpy)_3^{2+}$ solution when probe oiligonucleotide and target oilgonucleotide are hybridized, which shows similar quantity of light to that detected at a gold plate surface of 'a' even in the hybridized state. And, d indicates quantity of light detected by $Ru(bpy)_3^{2+}$ solution by processing doxorubicin in the hybridized oligonucleotide and washing, which shows that the doxorubicin binding to the hybridized oligonucleotide is not removed at a washing step and causes electrochemiluminescence. The quantity of light shown in 'd' is about two times of that shown at the a, b, and c. According to this, it can be known that electrochemiluminescnece is induced by intercalator. The result shows that detecting nucleic acid hybridization by the intercalator is more effective.

SECOND PREFERRED EMBODIMENT

Doxorubicin is used as intercalator and $Ru(phen)_3^{2+}$ is used as ruthenium derivative.

First, probe nucleic acid is fixed at a surface of a gold plate by using oligonucleotide solution having thiol group on 5'-phosphate (HS-C6-5'ACTCGCAAGCACCCTAT-CAGGC 3'). For the fixation, the gold plate is put to a tube and solution including 10 μm oligonucleotide and 10 mM NaCl is put to the tube, thereby processing for one day (about 10 hours) at a temperature of 37° C. The gold plate in which oligonucletide is ascended to a monomolecular layer is washed by phosphoric acid solution and immersed into 5×SSC buffer solution (sodium chloride of 750 mM, sodium citrate of 75 mM, and pH of 7.0) including 1 μm oligonucleotide having a complementary base sequence (5'-GCCTGATAGGGTGCTTGCGAGT-3'), thereby hybridizing for one day (about 10 hours) at a temperature of 37° C. Then, 1 ml doxorubicin solution dissolved in phosphoric acid buffer (pH 7.4) is added on the hybridized oligonucleotide, then reacted at the room temperature for about 30 minutes, thereby binding the doxorubicin to the oligonucleotide. After the reaction, the doxorubicin and the oligonucleotide are washed by 1×SSC buffer or phosphoric acid buffer solution (pH7.4), thereby removing unhybridized doxorubicin. A sample bound with doxurubicin and $Ru(phen)_3^{2+}$ solution of 1 ml dissolved in the phosphoric acid solution (pH7.4) are added to a measurement container, and a voltage of +1.19 is applied on the electrode 1 in a state that doxorubicin is binding, thereby detecting a change of quantity of light for time by an optical detector.

Figure 6:
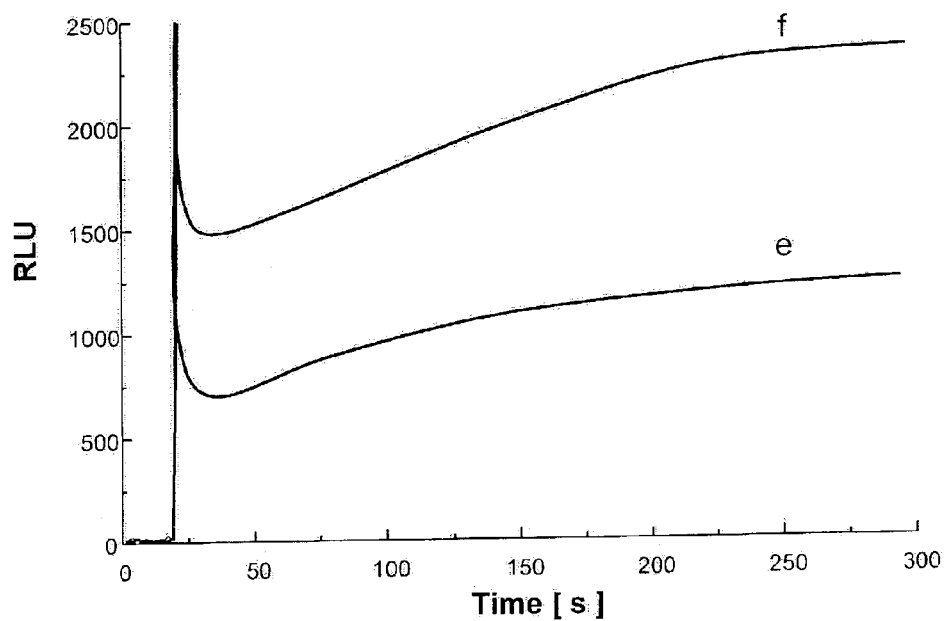
FIG. 6 shows a hybridization detection result of nucleic acid using doxorubicin and Ru(bpy)$_3^{2+}$ solution, in which e indicates quantity of light detected after reacting doxorubicin with probe nucleic acid and then washing, f indicates quantity of light detected after processing doxorubicin to the hybridized nucleic acid and then washing.

FIG. 6 shows a result of oxidation-reduction reaction between doxorubicin and $Ru(phen)_3^{2+}$ detected by an optical detector. In FIG. 6, e indicates quantity of light detected at the $Ru(phen)_3^{2+}$ solution after reacting oligonucleotide with doxorubicin and then washing. The quantity of light is shown a little more than that of 'a' in FIG. 5, which tells that electrochemiluminescence is generated by a reciprocal reaction between ruthenium and probe nucleic acid. f shows electrochemiluminescence detected at the $Ru(phen)_3^{2+}$ solution when the nucleic acid is hybridized and doxorubicin is intercalated. In that case, the doxorubicin is binding to the hybridized oligonucleotide and not removed from the oligonucleotide in a washing step. Also, it can be known that light is generated by inducing electrochemiluminescence of ruthenium.

THIRD PREFERRED EMBODIMENT

Daunorubicin is used as intercalator and $Ru(bpy)_3^{2+}$ is used as ruthenium derivative.

First, probe nucleic acid is fixed at a surface of a gold plate by using oligonucleotide solution having thiol group on 5'-phosphate (HS-C6-5'ACTCGCAAGCACCCTAT-CAGGC 3'). For the fixation, the gold plate is put to a tube and solution including oligonucleotide of 10 μm and NaCl of 10 mM is put to the tube, thereby processing for one day (about 10 hours) at a temperature of 37° C. The gold plate in which oligonucleotide is ascended to the monomolecular layer is washed by phosphoric acid solution and immersed into 5×SSC buffer solution (sodium chloride of 750 mM, sodium citrate of 75 mM, and pH of 7.0) including 1 μm oligonucleotide having a complementary base sequence (5'-GCCTGATAGGGTGCTTGCGAGT-3'), thereby hybridizing for one day (about 10 hours) at a temperature of 37° C. Next, 1 ml daunoorubicin solution dissolved in phosphoric acid buffer (pH 7.4) is added on the hybridized oligonucleotide, then reacted at the room temperature for about 30 minutes, thereby binding the daunorubicin to the oligonucleotide. After the reaction, the daunorubicin and the oligonucleotide are washed by 1×SSC buffer or phosphoric acid buffer solution (pH7.4), thereby removing unhybridized daunorubicin. A sample bound with daunourubicin and $Ru(bpy)_3^{2+}$ solution of 1 ml dissolved in the phosphoric acid solution (pH7.4) are added to a measurement container, and a voltage of +1.19 is applied on the electrode 1 in a state that daunorubicin is binding, thereby detecting a change of a quantity of light for time by an optical detector.

Figure 7:
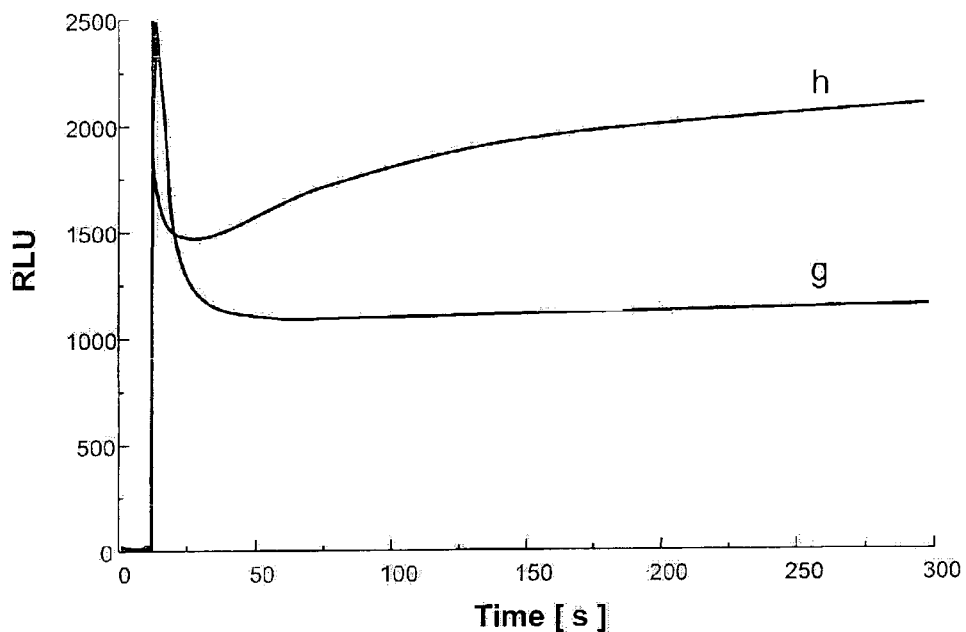
FIG. 7 shows a hybridization detection result of nucleic acid using daunorubicin and Ru(bpy)$_3^{2+}$ solution, in which g indicates quantity of light detected after reacting daunorubicin with probe nucleic acid and then washing, h indicates quantity of light detected after processing daunorubicin to the hybridized nucleic acid and then washing.

FIG. 7 shows a result of oxidation-reduction reaction between daunorubicin and $Ru(bpy)_3^{2+}$ detected by an optical detector. In FIG. 7, g indicates quantity of light detected at the $Ru(bpy)_3^{2+}$ solution after reacting 1 ml daunorubicin for 30 minutes at the room temperature in oligonucleotide state and then washing. The quantity of light is shown a little more than that of 'a' in FIG. 5, which tells that electrochemiluminescence is generated by a reciprocal reaction between ruthenium and probe nucleic acid. h shows electrochemiluminescence detected at the $Ru(bpy)_3^{2+}$ solution when the oligonucleotide is hybridized and doxorubicin is intercalated. The h shows quantity of light corresponding to two times of 'g' of FIG. 7, thereby knowing that a detection is performed more effectively. Also, when compared with the 'g' in which quantity of light is shown in a state that probe oligonucleotide and ruthenium are reacted each other weakly, the 'h' shows that the oligonucleotide hybridized with the probe olionucleotide are effectively separated by a high influence of intercalator.

In a method for detecting target nucleic acid by transition metallic complex in accordance with the conventional electrochemiluminescence, intercalation is not used. Also, in a method for detecting by binding ruthenium or tripropylamine to probe nucleic acid, a sample processing was complicated and a detection sensitivity was not good.

Figure 8:
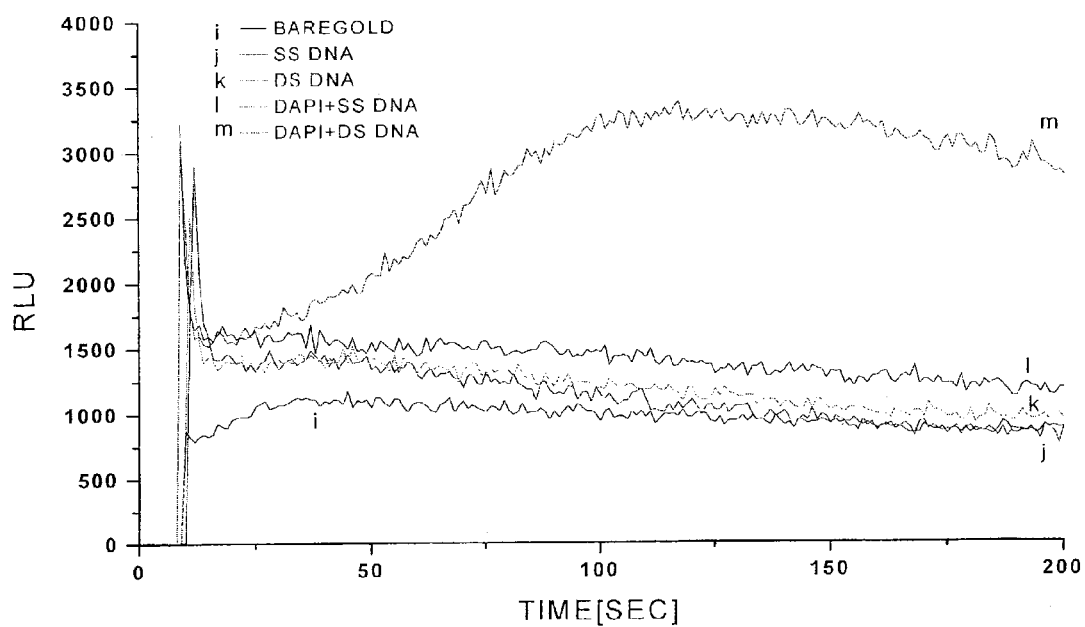
FIG. 8 shows a hybridization detection result of nucleic acid using DAPI, wherein I, j, k, l and m are the quantities of light corresponding to a bare gold plate without DAPI, single stranded DNA (ss DNA) without DAPI, double stranded DNA (ds DNA) without DAPI, ss DNA with DAPI, and ds DNA with DAPI, respectively.

FIG. 8 shows that the hybridized nucleic acid (DS DNA) can be distinguished from the non-hybridized probe nucleic acid (SS DNA), by intercalation of DAPI, wherein it can be shown that the light quantity of the hybridized DS DNA intercalated by DAPI is outstandingly higher than the other cases, such as bare gold, ss DNA without DAPI, ds DNA without DAPI, ss DNA intercalated by DAPI. From this fact, it can be found that DAPI is one of effective intercalators for detecting a result of nucleic acid hybridization.

However, in the present invention, by using intercalator, double-stranded nucleic acid bound complementarily can be effectively detected. Also, since intercalator is intercalated in double-stranded nucleic acid generated by a complementary reaction of the nucleic acid, a precise and selective detection is possible. Also, since fluorescent material such as Cy3 and Cy5 used in the conventional nucleic acid array is not required to label-react to probe nucleic acid or target nucleic acid, a detection process is fast and an additional complicated process is not required, thereby having a simple detection. Besides, since the transition metallic complex is detected by electrochemiluminescence, an external light source such as a laser or a lamp is not required and other optical components such as a filter and a polarizer are not required, thereby enabling a cheap detecting system and having a simple construction. Also, noise and scattering are not generated not by using light source such as a laser, thereby enabling a precise detection.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for detecting nucleic acid hybridization comprising the steps of:
    (1) fixing probe nucleic acid having thiol group on the position of 5'-phosphate on a surface of working electrode in a reaction container;
    (2) washing the surface of working electrode to which the probe nucleic acid is fixed, with phosphoric acid solution, followed by immersing into a buffer solution, which contains target nucleic acid having base sequences complementary to the probe nucleic acid, in order to allow hybridization to occur;
    (3) adding the buffer solution dissolved with intercalators to the hybridized nucleic acid, in order to bind the intercalators to the hybridized double-stranded nucleic acid;
    (4) removing any intercalators that remain unbound by washing with the buffer solution;
    (5) placing the working electrode, on which hybridization and the binding of the intercalator occurred, into a measurement container, followed by adding transition metallic complex that is dissolved in the buffer solution, and installing a reference electrode and a counter electrode; and
    (6) applying a voltage on the electrodes and inducing oxidation-reduction reaction of the transition metallic complex by the binding of the intercalator to the double-stranded nucleic acid, to thereby cause an electrochemiluminescence reaction.

2. The method for detecting nucleic acid hybridization of claim 1, wherein the intercalator is selected from the group consisting of doxorubicin, daunorubicin and DAPI.

3. The method for detecting nucleic acid hybridization of claim 1, wherein the transition metallic complex is [Ru(bpy)$_3^{2+}$] or [Ru(phen)$_3^{2+}$].

4. The method for detecting nucleic acid hybridization of claim 1, wherein an applied voltage ranges from +1.12 to +1.20 V.

5. The method for detecting nucleic acid hybridization of claim 1, wherein the nucleic acid is selected from the group constiting of oligonucleotide, DNA, RNA, PNA and cDNA.

6. A method for detecting nucleic acid hybridization comprising the steps of:
    (1) puffing a gold plate to a reaction container and fixing probe nucleic acid having thiol group on the position of 5'-phosphate on a surface of the gold plate;
    (2) washing the gold plate, to which the probe nucleic acid is fixed, with phosphoric acid solution and immersing into a buffer solution, which contains target nucleic acid having base sequences complementary to the probe nucleic acid, in order to allow hybridization to occur;
    (3) adding the buffer solution dissolved with intercalators to the hybridized nucleic acid in order to bind the intercalators to the hybridized double-stranded nucleic acid;
    (4) removing any intercalators that remain unbound by washing with the buffer solution;
    (5) placing the gold plate, on which hybridization and intercalator binding are performed, in the measurement container, adding transition metallic complex that is dissolved in the buffer solution, and then installing a working electrode, a reference electrode and a counter electrode; and
    (6) applying a voltage on the electrodes and inducing oxidation-reduction reaction of the transition metallic complex by the binding to double-stranded nucleic acid, to cause an electrochemiluminescence reaction.

7. The method for detecting nucleic acid hybridization of claim 6, wherein the intercalator is selected from the group consisting of doxorubicin, daunorubicin and DAPI.

8. The method for detecting nucleic acid hybridization of claim 6, wherein the transition metallic complex is [Ru(bpy)$_3^{2+}$] or [Ru(phen)$_3^{2+}$].

9. The method for detecting nucleic acid hybridization of claim 6, wherein an applied voltage ranges from +1.12 to +1.20 V.

10. The method for detecting nucleic acid hybridization of claim 6, wherein the nucleic acid is selected from the group consisting of oligonucleotide, DNA, RNA, PNA and cDNA.

* * * * *